(12) United States Patent
Sramek et al.

(10) Patent No.: US 8,496,650 B2
(45) Date of Patent: Jul. 30, 2013

(54) METHOD AND APPARATUS FOR PHOTOTHERMAL THERAPY WITH ADJUSTABLE SPATIAL AND/OR TEMPORAL BEAM PROFILE

(75) Inventors: Christopher K. Sramek, Stanford, CA (US); Daniel V. Palanker, Sunnyvale, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 607 days.

(21) Appl. No.: 12/653,652

(22) Filed: Dec. 15, 2009

(65) Prior Publication Data
US 2010/0168724 A1    Jul. 1, 2010

Related U.S. Application Data

(60) Provisional application No. 61/201,906, filed on Dec. 15, 2008.

(51) Int. Cl.
*A61B 8/18* (2006.01)
*A61N 5/06* (2006.01)
(52) U.S. Cl.
USPC ........................ 606/4; 3/13; 607/88
(58) Field of Classification Search
USPC ................. 606/3–6, 10–13, 16–19; 607/88, 607/89; 351/205–212; 128/898
See application file for complete search history.

(56) References Cited

U.S. PATENT DOCUMENTS

| | | | |
|---|---|---|---|
| 5,336,216 A | 8/1994 | Dewey | |
| 5,982,789 A | 11/1999 | Marshall et al. | |
| 6,016,227 A | 1/2000 | Hopkins et al. | |
| 7,413,572 B2 | 8/2008 | Eimerl et al. | |
| 8,187,257 B2* | 5/2012 | Lin et al. | 606/10 |
| 2001/0001818 A1* | 5/2001 | Hibst | 606/10 |
| 2004/0002694 A1 | 1/2004 | Pawlowski et al. | |
| 2005/0055015 A1 | 3/2005 | Buzawa | |
| 2006/0161145 A1 | 7/2006 | Lin et al. | |
| 2007/0173793 A1 | 7/2007 | Rathjen | |

OTHER PUBLICATIONS

Schulmeister et al., "Retinal thermal damage threshold studies for multiple pulses", Proc.. SPIE v. 6426, 2000.

* cited by examiner

*Primary Examiner* — Mohammed Hasan
(74) *Attorney, Agent, or Firm* — Lumen Patent Firm

(57) ABSTRACT

The safe therapeutic window for laser medicine tends to decrease as pulse length decreases. This problem is addressed by use of beam shapes and/or pulse shapes that improve temperature uniformity in the treated tissue. A beam shape with an adjustable on-axis intensity minimum improves spatial temperature uniformity in treated tissue. A pulse shape with a relatively intense early part (to set the temperature rise), followed by a less intense late part having decreasing intensity with time (to maintain a constant or nearly constant temperature rise) improves temporal temperature uniformity in the treated tissue. A therapeutic window (TW) of at least 3 is often required to provide a sufficient safety margin in practice. In one experiment, it was demonstrated that the minimum pulse length to provide a TW of 3 could be decreased from 20 ms to 10 ms following these principles.

16 Claims, 8 Drawing Sheets

METHOD AND APPARATUS FOR PHOTOTHERMAL THERAPY WITH ADJUSTABLE SPATIAL AND/OR TEMPORAL BEAM PROFILE

CROSS REFERENCE TO RELATED APPLICATIONS

This application claims the benefit of U.S. provisional patent application 61/201,906, filed on Dec. 15, 2008, entitled "Method and apparatus for photothermal therapy with adjustable spatial and temporal beam profile", and hereby incorporated by reference in its entirety.

GOVERNMENT SPONSORSHIP

This invention was made with Government support under contract number FA9550-04-1-0075 awarded by the Air Force Office of Scientific Research. The Government has certain rights in this invention.

FIELD OF THE INVENTION

This invention relates to phototherapy.

BACKGROUND

Laser medicine has been employed for treating eye disease for many years. For example, photocoagulation of the retina is the standard of care for several retinopathies. In photocoagulation, it is important to deliver the correct dose of energy to the treated locations. Doses that are too small will have little or no therapeutic effect, while doses that are too large can rupture the retina, or otherwise lead to excessive damage. In view of this criticality of the delivered dose, various approaches have been considered for improving optical therapy.

For example, in U.S. Pat. No. 7,413,572, measurements are performed at treatment sites that have already been treated. These results are then used to adjust the parameters of subsequent optical treatment pulses. In U.S. Pat. No. 5,336,216, changing the shape of a Gaussian beam to provide a sharp-edged spot on the target is considered. In U.S. Pat. No. 5,982,789, methods for increasing power stability of a pulsed diode-pumped frequency doubling system are considered.

However, not all problems in laser medicine can be addressed with conventional phototherapy approaches.

SUMMARY

One such problem results from the relatively recent interest in decreasing the pulse duration in phototherapy, which is conventionally in the range of 100-500 ms. A motivation for the use of shorter pulses is the success of Patterned Scanning Laser photocoagulation (e.g., as described in US 2006/0100677). In this approach, patterns of 4 to 50 exposures are delivered sequentially within the eye fixation time, with pulse durations in the range of 20 ms. These shorter exposures have been shown to be less painful and as efficacious as traditional retinal photocoagulation, while targeting the photoreceptor layer more selectively.

However, coagulation at shorter pulse durations increases the potential for photomechanical injury and rupture of Bruch's membrane, as it requires higher peak temperatures. Consequently, the safe therapeutic window, defined as the ratio of power for producing a rupture to that of mild coagulation, has been found to decrease with shorter exposures, approaching one at 1 ms. The application of shorter pulses in clinical practice is potentially desirable as it would decrease treatment time and patient discomfort. Thus, it would be beneficial to increase the safe therapeutic window for pulse durations shorter than 20 ms.

In the present application, this problem is addressed using two distinct approaches, which can be practiced separately or in combination. In the first approach, the spatial shape of the treatment beam is altered to have an adjustable on-axis intensity minimum to counteract heat diffusion and thereby produce a more uniform temperature distribution across the heated zone. In the second approach, the pulse temporal shape is altered to improve temperature rise uniformity in treated tissue during the pulse. For example, pulses can have a high and constant intensity first part (heating phase) followed by a second part where the intensity is lower and decreases during the second part in order to maintain a more constant temperature in the tissue. Both of these approaches have the beneficial effect of making the temperature distribution in the treated tissue more uniform (in space and/or in time). Experimental investigations have shown that these approaches increase the safe therapeutic window for short pulses.

DETAILED DESCRIPTION

To better appreciate the present work, it is helpful to first consider some general principles (section A), then proceed to a description of beam shaping experimental results (section B) and pulse shaping experimental results (section C).

A. Principles

Due to more rapid heat diffusion from the periphery of an irradiated zone than from its center, the central part of the irradiated zone has higher temperature, even if a flat (top-hat) beam profile is applied. Similarly, with a constant power during the pulse, tissue reaches its maximum temperature only at the end of the pulse. A key idea of the present application is to counteract heat diffusion by adjusting spatial and/or temporal beam parameters in such a way that constant temperature is achieved during a substantial fraction of the pulse duration, and also across a significant part of the laser beam.

A first embodiment of the present approach is an apparatus for optical therapy, where the apparatus includes a source of light and optics configured to receive radiation (i.e., light) from the source and to provide an output treatment beam having an on-axis intensity minimum with an adjustable modulation depth. Although practice of the invention does not depend critically on how this adjustable beam shape is achieved, one preferred approach makes use of multi-mode optical fiber. More specifically, an adjustable ratio of fundamental mode amplitude to higher order mode amplitude can be used to provide the adjustable modulation depth of the on-axis intensity minimum.

Figure 1A:
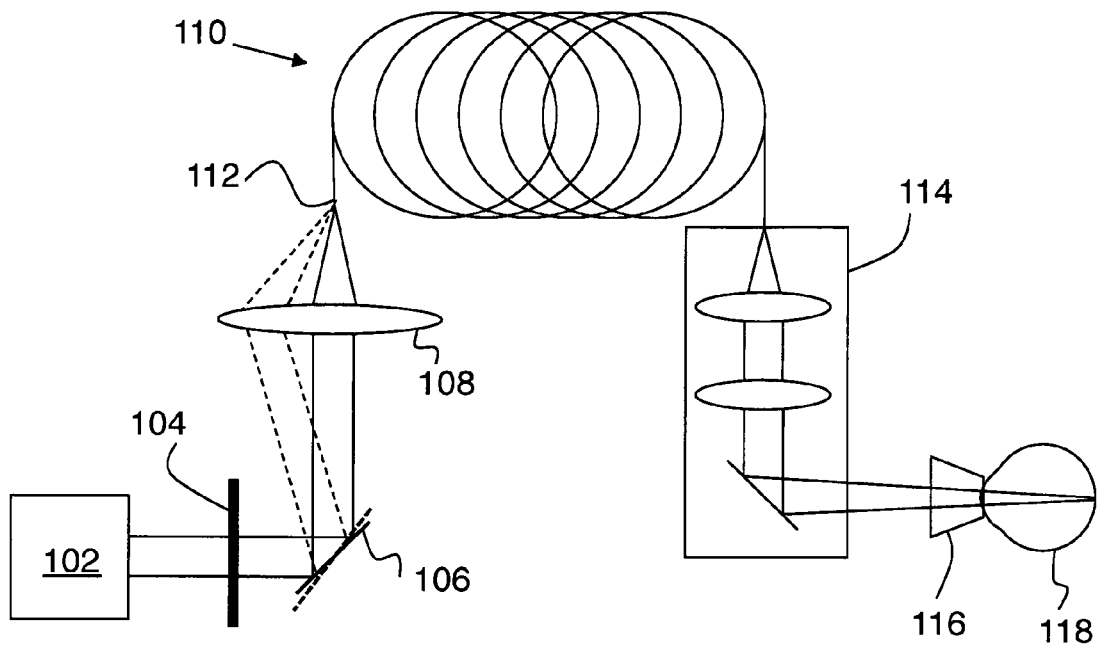
FIG. 1a shows an example of an embodiment of the invention.

The example of FIG. 1a shows one way to provide this adjustability. In this example, a source 102 emits radiation that is blocked or passed by a shutter 104. This radiation impinges on a mirror 106 that has an adjustable position. Radiation from mirror 106 is coupled to multi-mode fiber 110 by using a focusing lens 108 to couple to the fiber end face 112. Radiation emitted from fiber 110 is received by a fiber-adapted slit lamp assembly (schematically shown as 114), which collimates, directs and focuses the radiation to the desired location in an eye 118. A contact lens 116 can be employed to improve the coupling of the radiation to eye 118.

As shown on FIG. 1a, the radiation launch conditions at end face 112 can be altered by changing the position of mirror 106. For example, tilting mirror 106 changes the angle at which radiation is incident on end face 112 (dashed lines). A ring-shaped illumination pattern can be achieved by coupling the beam into the fiber end face at an angle (about 5° was used in one experiment) with respect to normal incidence. This particular coupling method results in excitation of a combination of the $TEM_{00}$ mode (the fundamental mode) and $TEM_{01}*$ mode (a higher order mode sometimes referred to as the "doughnut" mode) supported by the fiber.

The depth of the on-axis intensity minimum is preferably in a range from 0.1 to 0.9 of the maximum intensity of the treatment beam spatial pattern.

Figure 8:
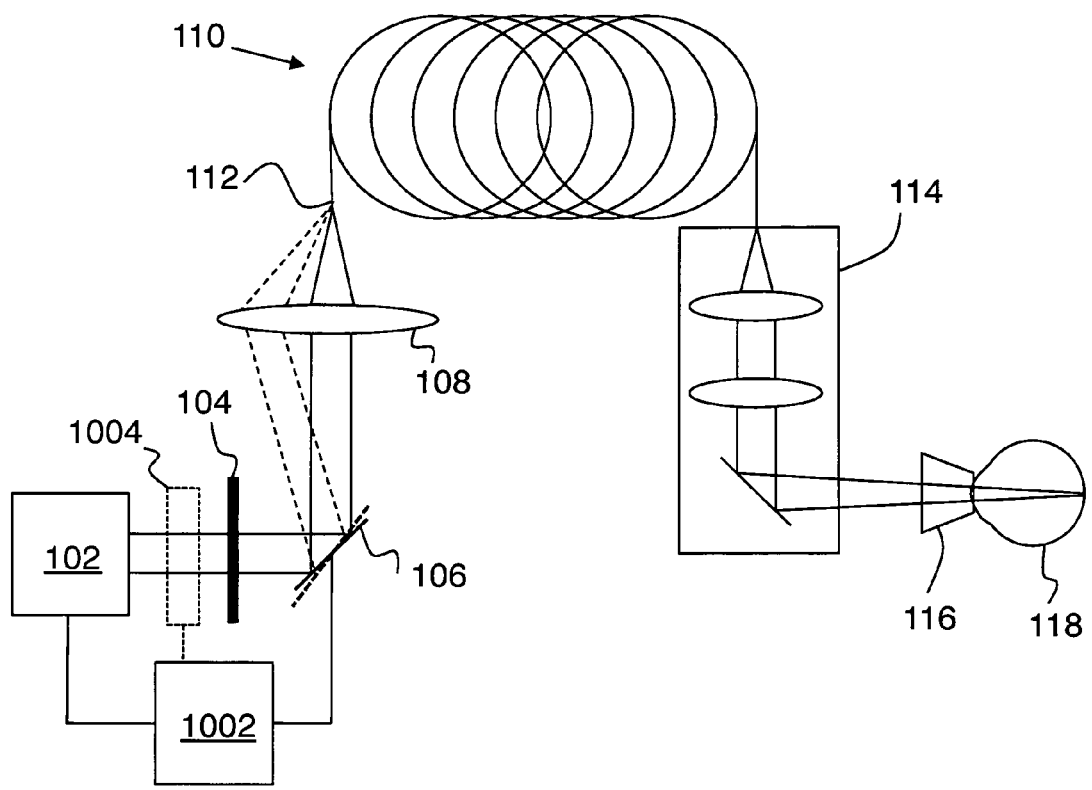
FIG. 8 shows an example of a further embodiment of the invention.

A capability of controlling pulse shape with greater flexibility can be added to this first embodiment. More specifically, a controller configured to provide the output treatment beam as a pulsed beam using optical radiation from the source can be added. The pulses each include an early part preceding a late part, where the early part has higher intensity than the late part. The modulation depth of the on-axis minimum can be held constant during a sequence of these shaped pulses. Alternatively, the modulation depth can change from one pulse to another of the pulses and/or within a pulse duration. FIG. 8 shows an example of suitable apparatus for this approach. FIG. 8 is similar to FIG. 1a, except that a controller 1002 is added to provide pulse shape control. Such pulse shape control can be provided by directly modulating the source 102 (e.g., by altering the drive current to a laser diode). Pulse shape control can also be provided by adding an optional external modulator 1004 that is controlled by controller 1002.

A second embodiment of the present approach is a method for optical therapy. In this method, shaped pulses of optical radiation are delivered to the target tissue. The shaped pulses each have an early part preceding a late part, where the early part is more intense than the late part. The late part of the pulse is at least 20% of the pulse duration and has a pulse shape selected to maintain a temperature rise at one or more points of the target tissue that is constant to within 10% during the late part. The intensity ratio of the late part relative to the early part can be made adjustable. Preferably the temperature rise is held constant to within 10% during the pulse late part at part of all of the illuminated target tissue. More preferably, the region of temperature uniformity is made as large as possible by optimizing pulse shape.

The capability of providing an on-axis beam minimum can be added to this second embodiment. The on-axis intensity minimum can have an adjustable modulation depth. This modulation depth can be adjusted during the pulses and/or from one pulse to the next.

Figure 4:
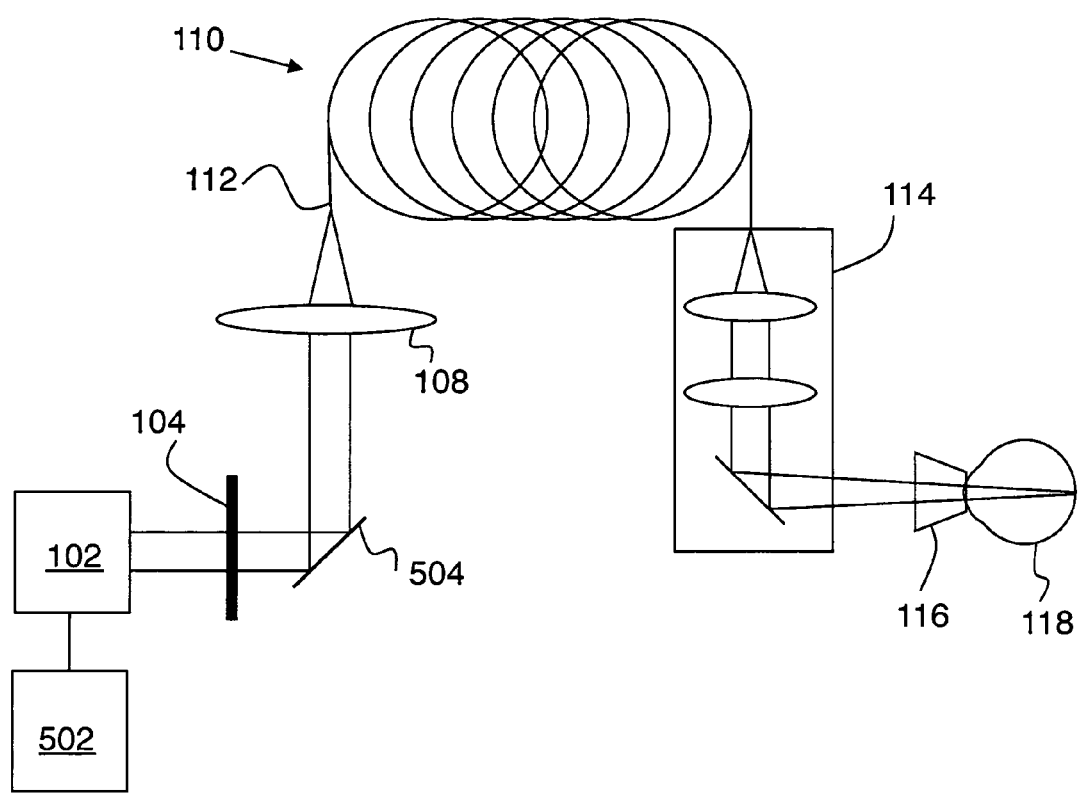
FIG. 4 shows an example of another embodiment of the invention.

A third embodiment of the invention is an apparatus for optical therapy. This apparatus includes an optical source and a controller configured to provide a pulsed output treatment beam. The pulses each have an early part, to heat the tissue to the target temperature, followed by a late part, for maintaining a constant target temperature. The early part is at least 10% of the pulse duration, has an intensity that is constant to within 10% during the early part, and has higher intensity than the late part. The late part is at least 20% of the pulse duration and has a decreasing intensity during the late part. FIG. 4 shows an example of suitable apparatus for practicing this embodiment. This example is like the example of FIG. 1a, except that adjustable mirror 106 of FIG. 1a is replaced with a fixed mirror 504, and a pulse shape controller 502 (providing direct modulation of source 102) is added. External modulation (e.g., as shown on FIG. 8) is also an option here. The intensity ratio of the late part relative to the early part is preferably in a range from 0.1 to 0.9.

The capability of providing an on-axis beam minimum can be added to this third embodiment. FIG. 8 shows an example of suitable apparatus for this possibility. Here also, the modulation depth of the intensity minimum can be altered during pulses and/or from one pulse to the next.

In the preceding description, the early and late parts of the pulses can be parts of a single continuous pulse "body" (i.e., excluding pulse rising and falling edges, in cases where the rising and/or falling edges of a pulse can be distinguished from the pulse body). In a high frequency pulse train, when tissue temperature does not significantly decrease between the pulses, one or several pulses at the beginning of the train can be the "early" part, heating the tissue to the target temperature, and the following pulse(s) of the train can be the "late" part, maintaining constant temperature. For shaped pulses, the definition of pulse duration is more complicated than for simple square pulses. Although full-width half-maximum (FWHM) is often regarded as the pulse duration, this definition of pulse duration may not be satisfactory for shaped pulses. Defining duration as the full-width tenth-maximum (FWTM) may be more appropriate in certain cases (e.g., if the late part has intensity less than half the intensity of the early part).

B. Experimental Demonstration of Beam Shaping

B1. Introduction

As indicated above, it is desirable to increase the therapeutic window in order to allow for shorter duration pulses to be safely used in photocoagulation. One approach to this end is to modify the shape of the treatment beam. With conventional top-hat or Gaussian beam profiles, heat diffusion during the pulse results in an elevated temperature at the beam center. Such over-heating results in a higher maximum temperature than necessary to produce the desired retinal coagulation, and increases the probability of rupture. A beam shape with a lower intensity in the center compensates for the effects of thermal diffusion, resulting in a more uniform temperature profile and thermal damage zone. This absence of central overheating is expected to result in a wider therapeutic window.

The amplitude and diameter of the optimal central depression is dependent on the pulse duration and beam size. In pulsed laser heating, a characteristic length scale for temperature elevation is the diffusion length $L_D=(4 k\tau)^{1/2}$, where k is the thermal diffusivity of the medium ($1.5\times10^{-7}$ m$^2$/s for liquid water) and τ is the pulse length. With pulse durations in the range of 1-100 ms, this length is on the order of 20-200 µm. The central depression diameter needs to account for the desired duration at which the temperature should be uniform. Precise estimation of the optimal beam shape can be aided by solving the heat conduction equation, which can account for differences in heat deposition in various retinal layers, inhomogeneities due to pigmentation variation, and convective cooling due to perfusion. Due to these factors, computational modeling can greatly help in calculating optimal beam parameters.

We performed finite-element modeling in conjunction with in vivo experiments to evaluate the safety of ring-beam photocoagulation relative to a conventional top-hat beam shape.

B2. Methods

B2a. Instrument

Figure 1B:
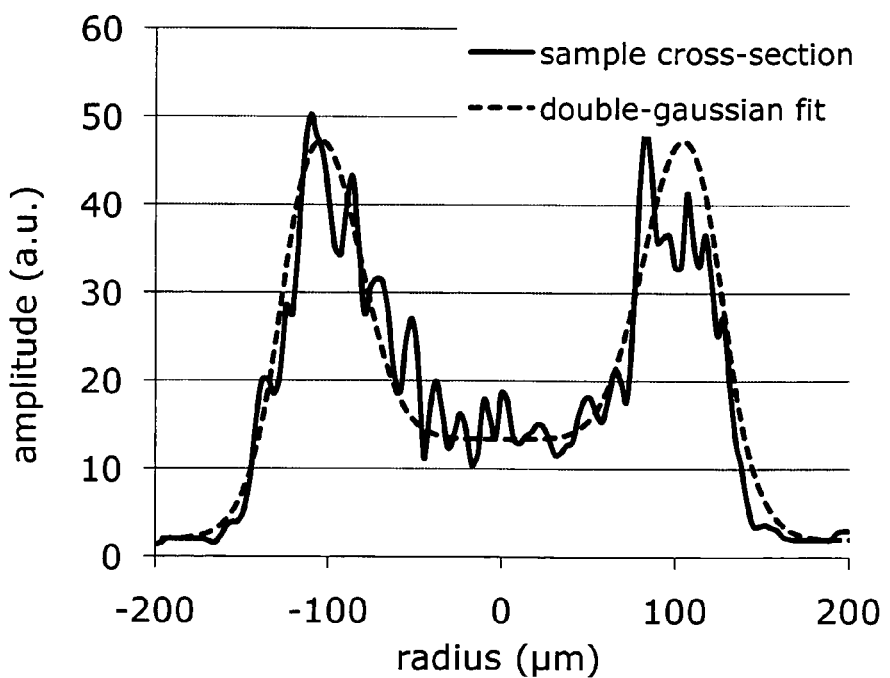
FIG. 1b shows a beam profile employed in an experimental test of an embodiment.

A modified slit lamp (Zeiss, SL 130) was used to support the laser delivery system and provide a view of the fundus (FIG. 1a). The optical radiation from a diode-pumped continuous-wave frequency-doubled (532 nm wavelength) Nd:YLF laser 102 (MP532-3W, Monocrom) was coupled into a 200 µm core diameter multimode optical fiber 110 (FG200LCC, Thorlabs, Inc., Newton, N.J.). A ring-shaped illumination pattern was achieved by coupling the beam into the fiber tip 112 at an angle)(~5° with respect to normal incidence. This particular coupling method results in excitation of a combination of the $TEM_{00}$ (fundamental) and $TEM_{01}^*$ ("doughnut") modes supported by the fiber. A plane near the exit surface of the fiber was imaged through an adapter attached to the slit lamp (LaserLink, Lumenis, Santa Clara, Calif.) onto the retina. At the aerial image plane of the slitlamp microscope, the full-width-half-max (FWHM) spot size measured 260 µm, with the laser irradiance transition from 10% to 90% occurring over 35 µm on the external edge of the ring. Variation of the beam irradiance due to speckling along a circular contour coinciding with the irradiance maximum did not exceed 20%. A central amplitude modulation of 75% was used. (FIG. 1b). The aerial beam shape was imaged before every experiment to ensure that the same combination of the fiber modes was achieved.

A graphical user interface (LabView, National Instruments Corp., Austin, Tex.) for the laser power supply (DS11, OSTech GmbH, Berlin) allowed for adjustment of duration and power, and a foot pedal activated the laser. A mechanical shutter was used to cut off the first 15 ms of the laser output to limit initial transient oscillations. This system was used to produce square pulses of 2-100 ms in duration, with intensity variations during the pulse of less than 10%. For comparison a PASCAL® photocoagulator (Optimedica, Santa Clara, Calif.) was used to produce a top-hat beam (200 µm aerial spot-size) and pulse durations in the range of 2-100 ms.

B2b. Experimental Methods

14 Dutch Belted rabbits (weight, 1.5-2.5 kg) were used in accordance with the Association for Research in Vision and Opthalmology Resolution on the Use of Animals in Ophthalmic and Vision Research with approval from the Stanford University Animal Institutional Review Board. Ketamine hydrochloride (35 mg/Kg), xylazine (5 mg/Kg) and glycopyrrolate (0.01 mg/Kg) were used for anesthesia. Pupil dilation was achieved by 1 drop each of 1% tropicamide and 2.5% phenylephrine hydrochloride, and topical tetracaine hydrochloride 0.5% was used for local anesthesia. Both eyes of each rabbit were treated with ring-beam and top-hat exposures to allow for direct comparison of the relative safety of each treatment on an eye-to-eye basis. Exposures of 2, 5 and 10 ms were placed in one eye of each animal and 20, 50 and 100 ms exposures were placed in the fellow eye.

The threshold powers of mild coagulation and rupture at each of these pulse durations were measured for the two beam shapes. Between 12 and 36 separate lesions were administered per eye for each beam shape and the three pulse durations. Power was titrated to produce lesions with clinical grades ranging from invisible to rupture. A standard retinal laser contact lens (OMSRA-S; Ocular Instruments, Bellevue, Wash.) was placed onto the mydriatic eye using hydroxypropyl methylcellulose as a contact gel. Taking into account the combined magnifications of the contact lens and rabbit eye of 0.66 the aerial images of 260 µm for the ring-beam and 200 µm for the top-hat corresponded to retinal spot sizes of 170 and 132 µm, respectively.

The clinical appearance of the laser lesions was graded by one observer within 3 seconds of delivering the laser pulse by means of the following scale: barely visible, mild, intense, and rupture. A barely visible lesion (often referred to as a minimally visible lesion, or MVL) was one that just crossed the limit of clinical detection, whereas a mild lesion was described as one that produced more significant blanching but no whitening. An intense lesion had an area of central whitening, with or without a ring of translucent edema. A rupture was assumed when a vapor bubble or discontinuity in retinal architecture was visualized with or without bleeding. Threshold powers for mild coagulation and rupture were calculated by Probit analysis (MATLAB® 7.4, MathWorks, Natick, Mass.). The results were analyzed in terms of mean improvement in safe therapeutic window.

To examine general histological character of the ring-beam lesions, mild coagulation lesions were produced in 2 eyes with pulse durations ranging from 5 to 100 ms. Eyes were enucleated after 1 day and fixed in 1.25% glutaraldehyde/1% paraformaldehyde in cacodylate buffer at pH 7.4. It was then postfixed in osmium tetroxide, dehydrated with a graded series of ethanol, and embedded in epoxy resin. Sections of 1 µm thickness were stained with toluidine blue and examined by light microscopy.

B2c. Computational Model

A finite-element model of retinal heating and coagulation constructed in the COMSOL Multiphysics 3.5 computational package was used to predict safe therapeutic window for the two experimental beam shapes at various pulse durations. This model approximated the retina as a series of homogeneous absorbing layers and coupled an axi-symmetric heat conduction model with an Arrhenius damage model. Layer absorption coefficients and damage model parameters were taken from experimental data and literature.

Several important modifications of the original model were implemented in this study. Ring-beam images from each in vivo experiment were normalized to their surface integral and a fit function of the form:

$$I(r) = A_0\left(\exp\left(-\left(\frac{r-r_0}{w_0}\right)^2\right) + \exp\left(-\left(\frac{r+r_0}{w_0}\right)^2\right)\right) + A_1\left(1 + \text{erf}\left(\frac{r_1-r}{w_1}\right)\right) \quad (1)$$

was selected in order to account for both the $LP_{01}$ and $LP_{11}$ radial modes in the fiber, where $A_0, A_1, r_0, r_1, w_0$ and $w_1$ are fit parameters. A numerical optimization for the 6 parameters was performed in MATLAB® 7.4 for each beam image, and average parameter values were used to give a functional description of the irradiance distribution on the retina. A sample ring-beam profile and the average fit are shown in FIG. 1b. The original error-function fit to the in vivo beam shape measured in the original model was used for the top-hat beam computations:

$$I(r) = A_2\left(1 + \mathrm{erf}\left(\frac{r_2 - r}{w_2}\right)\right) \quad (2)$$

Although the radial distributions in equations 1 and 2 do not match the Laguerre-Gaussian form used to describe modes in an optical fiber, these functions provided the best fit to the measured beam profiles in the focal planes of the experimental optical systems.

An important aspect of the original model was the presence of a central circular "hotspot" in the RPE layer of higher absorption coefficient ($\sim 4 \cdot \alpha_{RPE}$). This feature modeled worst-case local temperature variations due to cell-to-cell RPE pigmentation non-uniformities, and significantly increased peak temperature for short duration pulses. It was supported by measured variability of the RPE pigmentation, and its inclusion resulted in good match of temperatures computed from in vivo rupture threshold data with the estimated vaporization threshold of 180° C. For a ring-shaped beam, a centrally located hotspot does not correspond to the expected worst-case temperature variation. Rather a hotspot located at the irradiance maximum, centered along the "peak" of the ring will result in maximum temperature rise.

However, this off-center location destroys axial symmetry; to include this feature in the axi-symmetric model, an annular hotspot was considered. To find annulus parameters, a simplified 3D retinal heating model was constructed in COMSOL Multiphysics 3.5 consisting of absorbing RPE (4 μm thickness) and choroidal (70 μm) layers with the same absorption coefficients as the previous model. Using the functional fit to the measured ring-beam distribution and pulse durations from 1-100 ms, peak temperature was calculated for two geometries: (a) a 22 μm diameter circular hotspot centered on the irradiance maximum of the beam (full 3-D model), and (b) an annular hotspot of the same elevated absorption coefficient and variable width, with the center of the annulus strip at the irradiance maximum (2-D axi-symmetric model). Optical power was chosen such that the peak temperature at all durations was 180° C. An annular width of 9 μm was found to provide the closest approximation to the over-heating due to the 22 μm off-center circular hotspot.

Another important modification to the original model was the addition of a measure of opthalmoscopic lesion visibility. The original model predicted zones of acute cellular damage using the Arrhenius integral, but did not relate this value to clinical lesion appearance, which is necessary for estimating coagulation thresholds. Lesion grades can be modeled as different levels of light scattering from the retina. The optical scattering coefficient of coagulated retina increases due to disruption of the nominally ordered, translucent cells and cellular layers. It was assumed that the retinal blanching observed with mild coagulation occurs when damage exceeds a certain depth into the retina, at some minimally visible spot diameter. To estimate this width and depth, Arrhenius maps were calculated corresponding to mild coagulation grades from measured in vivo threshold powers with a top-hat beam at pulse durations in the 5-100 ms range. Contours corresponding to an Arrhenius integral of unity were extracted from these maps. The threshold width and depth was calculated as the point with minimum distance between all contours.

With these modifications, both mild coagulation and rupture threshold powers could be estimated in the model for top-hat and ring-shaped treatment beams. Arrhenius maps were calculated and mild coagulation threshold was computed using the described metric, while rupture threshold was estimated as the power necessary to bring peak temperature up to 180° C. with the inclusion of the circular or annular hotspot. Safe therapeutic window (the ratio of these thresholds) was computed as a function of duration.

B3. Results

Photographic representations of acute ring-beam retinal coagulation lesions corresponding to mild coagulation thresholds with pulse durations from 2 to 100 ms were analyzed. Ring lesions with pulse durations of 10 ms and longer have a region of central blanching, while shorter duration ring lesions do not, indicating that temperature rise in the center due to heat diffusion was not sufficient to affect the center of the beam similarly to the periphery. Moreover, lesions at all durations appear distinctly annular, indicating that the 75% depth of modulation used did not result in uniform radial coagulation at any duration. However, sample histological sections of these lesions all show disruption of the photoreceptor layer in the beam center. This is likely due to secondary tissue changes occurring between lesion formation and enucleation (~24 hours post-treatment).

Figure 2:
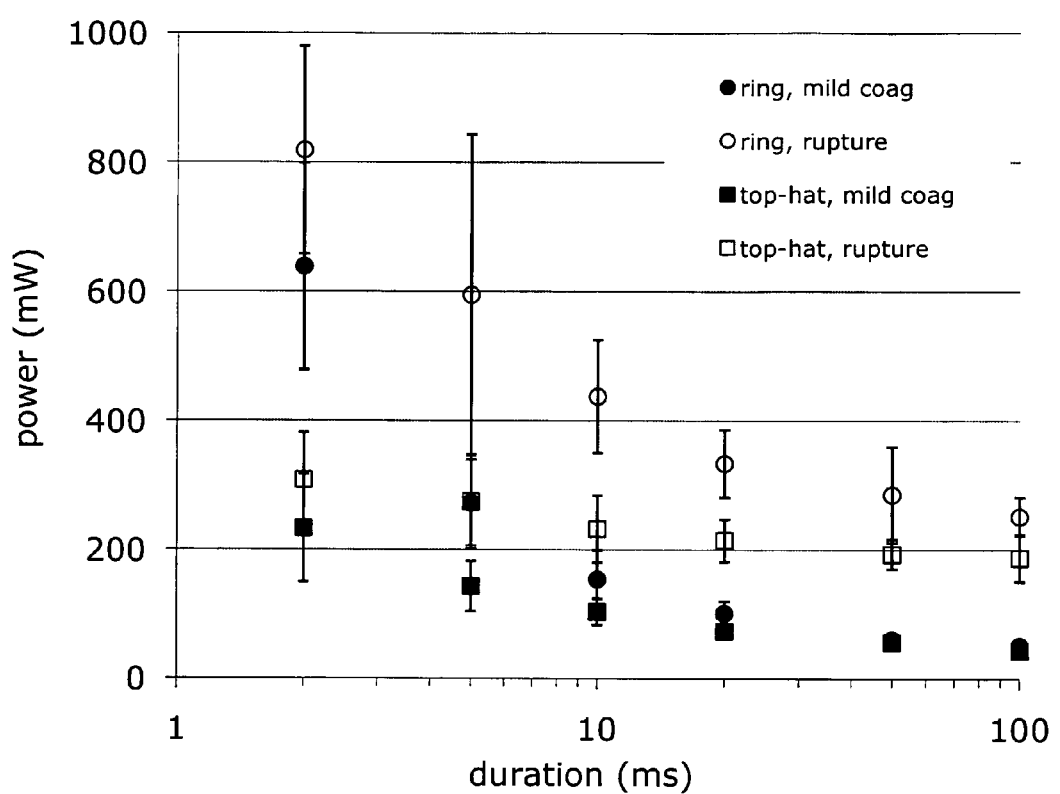
FIG. 2 shows mild coagulation and rupture thresholds for ring and top-hat beams as a function of pulse duration.
Figure 3:
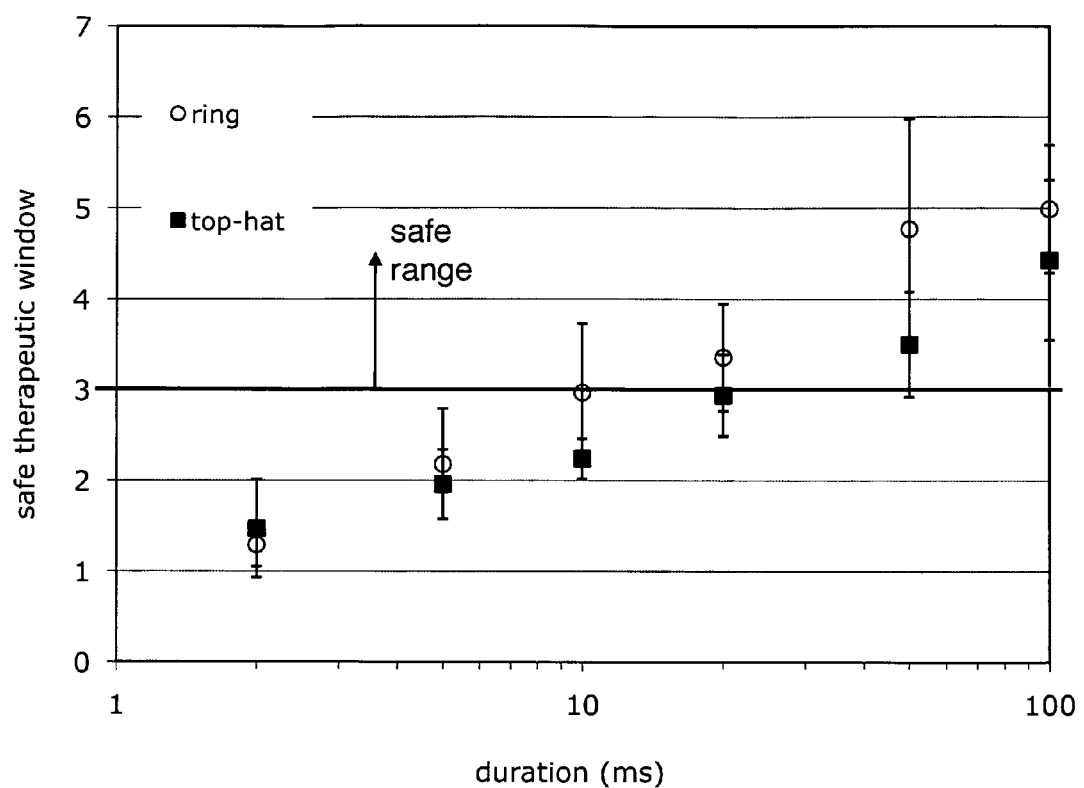
FIG. 3 shows safe therapeutic window as a function of pulse duration for ring and top-hat beams.

Mild coagulation and rupture threshold powers are shown in FIG. 2. Error bars indicate standard deviation in threshold measurements over 14 measurements. Average Probit slope (ED84/ED50) for the threshold measurements was 1.09 for the ring-shaped beam and 1.07 for the top-hat beam. The mean safe therapeutic window appeared to increase logarithmically with pulse duration for both beam shapes (FIG. 3), similarly to previous measurements. An improvement in therapeutic window was observed at all durations between 5 ms and 100 ms. The therapeutic window is expected to have a ratio statistical distribution, with the underlying threshold laser powers following correlated normal distributions. This ratio distribution deviates significantly from normal, making non-parametric hypothesis testing preferable. A paired permutation test was performed in MATLAB® 7.4 for the null hypothesis that the measured therapeutic windows came from the same distribution. The increase in therapeutic window (TW) was found to be statistically significant ($p<0.05$) for 10, 20 and 50 ms durations. The mean TW increase for 10 ms was +0.73 (95% CI: [0.27, 1.17]) while the increases for 20 ms and 50 ms were +0.42 [0.06, 0.77] and +1.27 [0.30, 2.22], respectively. These corresponded to percent-increases of 32.6% 14.3% and 36.3% over top-hat beam TW for 10, 20 and 50 ms durations, respectively. A small (<13%), statistically insignificant mean increase in TW was measured for 5 and 100 ms pulse durations, while a small decrease was observed for 2 ms. Thresholds from the model were found to deviate less than 14% on average from the measured values.

B4. Discussion

The goal of this work was to evaluate potential improvements in safety during short-pulse photocoagulation with a ring-shaped beam. The measured improvement in safe therapeutic window for 10-50 ms pulse durations indicates that this is possible. While the beam shape used in this study was a product of experimental convenience (maximizing power coupling into the ring mode) rather than optimization, the presence of a central depression had the desired effect for pulse durations where heat had adequate time to diffuse into the center. The measured ring-beam had a retinal peak-to-center distance of 69 μm, while the heat diffusion length in water for a 5 ms pulse is $L_D=54$ μm, indicating that heat produced along the peak of the ring is not expected to reach the center at this duration. In fact, maxima along the ring acts as an annular hot-spot, increasing the likelihood of rupture at short durations. This appears to be the reason for decreased therapeutic window at 2 ms. On the other hand, the diffusion length for a 10 ms pulse is 75.6 μm, indicating that the desired compensation for central overheating occurs to some degree at this duration. At very long pulse durations, heat is expected to diffuse across the entire beam diameter ($L_D$=239 μm at 100 ms); central overheating may then occur for certain modulation depths, negating the expected benefit from the central depression.

As in most in vivo measurements, several factors limited the accuracy in determination of threshold powers for coagulation and rupture. Measurement of the coagulation threshold is inherently a subjective process, and the distinction between a minimally visible lesion and mild coagulation is particularly sensitive to the judgment of the clinician. While the MVL threshold is more objective, as it depends solely on visibility rather than lesion character, the mild coagulation threshold is more clinically relevant and more familiar as a photocoagulation endpoint to the clinician. We attempted to control for subjectivity by using the same lesion judgment criteria for both beam types, pairing threshold measurements by placing both types of lesions in each eye, and using a single observer for all experiments.

Another aspect affecting threshold measurements is focal errors during treatment. Although the use of a parfocal photocoagulation system and contact lens provides for a large depth of focus, errors in focusing are inevitable during photocoagulation. Focusing will vary slightly from exposure to exposure, with the degree of defocusing depending upon the skill and fatigue of the surgeon and the animal's level of anesthesia. The ring-shaped beam will defocus in a different manner than a top-hat beam: for positive or negative focal errors, the ring beam central modulation decreases while the top-hat beam become more Gaussian in shape. Although broadening of the beam will likely result in increased TW relative to the in-focus case for both beam, the lack of central overheating for the ring beam may make it less sensitive to defocusing.

Other limitations on threshold measurements also relate to variations in laser energy deposition. RPE pigmentation varies by about a factor of two across a population, between species as well as across the fundus, with variations as high as a factor of three from macula to periphery. Paired therapeutic window measurements and averaging over multiple test eyes helps control for this variation. Laser pulse energy varies as a function of pulse duration and shot-to-shot due to intensity fluctuations of 10% and mechanical shutter timing jitter of ~300 μs. Direct measurement of laser pulse energy variation before each experiment allowed for this uncertainty to be included in the Probit analysis.

Practical clinical implementation of ring-beam photocoagulation may entail some modifications to the system used in this study. Production of the ring mode in this example is based on a change in coupling angle of the laser into the fiber. However, system stability should be considered, since the mode structure and coupled power are sensitive to movements of the fiber. Alternative methods for shaping the beam can be employed, such as masking the fiber tip or using spatial light modulators.

Further improvements might be realized by allowing the beam shape to evolve during the pulse, potentially by sweeping the coupling angle. A full spatiotemporal optimization of the beam evolution may result in a constant temperature maintained throughout the lesion, providing maximum coagulation at a given peak temperature.

Important clinical implications will arise if the measured improvement in safe therapeutic window can be duplicated in human subjects. As mentioned previously, pigmentation varies across the fundus, which requires a safe therapeutic window of on the order of three for any clinically applicable treatment. Photocoagulation with a ring beam allows for a therapeutic window of three to be achieved at 10 ms rather than 20 ms with a top-hat beam. This reduction in safe pulse duration would allow for up to a two-fold increase in the number of lesions placed during the eye fixation time with patterned scanning photocoagulation, halving the overall treatment time. It would also reduce destruction of the neural retina and decrease perceived pain due to less significant heat diffusion, making for a marked improvement over current photocoagulation standards.

C. Experimental Demonstration of Pulse Shaping

C1. Introduction

Figure 5A:
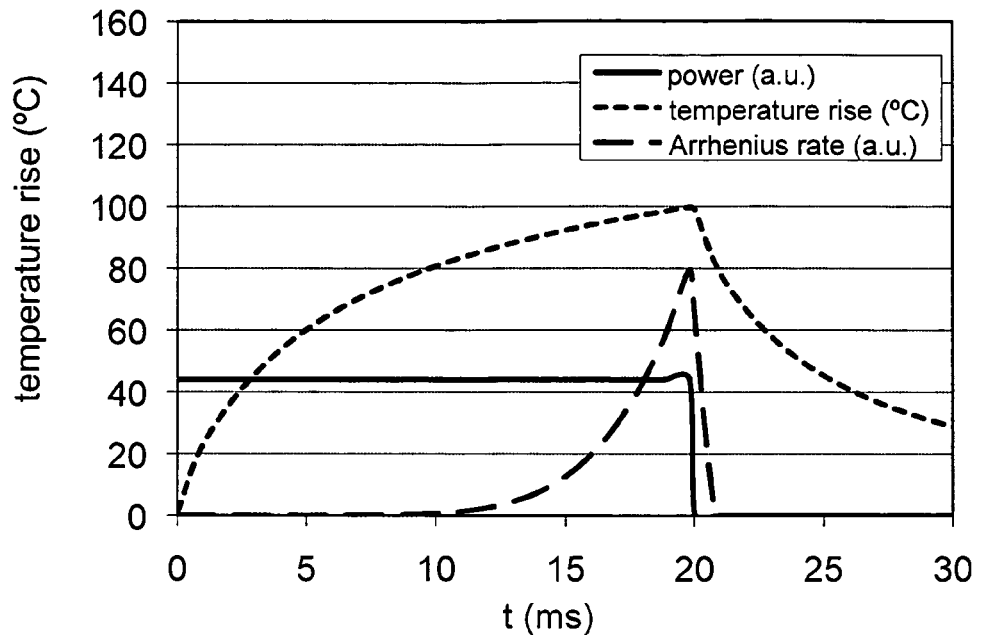
FIGS. 5a-b show pulse power, temperature rise and Arrhenius rates for a square pulse (FIG. 5a) and a shaped pulse (FIG. 5b).

As indicated above, it is desirable to increase the therapeutic window in order to allow for shorter duration pulses to be used in photocoagulation. One approach to this end is to modify the temporal structure of the pulse. Conventional pulses of constant power (square pulse shape) result in an increasing temperature during the pulse, asymptotically approaching a steady-state value for long exposures. Thermal cellular damage in the millisecond regime is often described using the Arrhenius model. It assumes a decrease in concentration of viable cells $D(\tau)/D_0$ as an exponential integral of the temperature time-course:

$$\Omega = A \int_0^\tau \exp\left(-\frac{E^*}{R \cdot T(t)}\right) dt = -\ln\left(\frac{D(\tau)}{D_0}\right) \quad (3)$$

where $E^*$ is the activation energy, A is the rate constant, and R is the gas constant. The increasing temperature with time produced by a square laser pulse leads to an exponential increase in the reaction rate at the end of the pulse, while most of the pulse duration does not effectively contribute to the tissue coagulation, as illustrated in FIG. 5a. This effect is particularly relevant for pulse durations shorter than the time constant corresponding to the steady-state condition, which is determined by the laser spot size. For a beam diameter L the diffusion time is on the order of $\tau_d = L^2/4$ k where k is the thermal diffusivity ($1.5 \times 10^{-7}$ m²/s for liquid water). For example, a 120 μm beam corresponds to a diffusion time $\tau_d = 24$ ms. Temperature reaches an approximate steady-state distribution with pulse durations greater than $\tau_d$.

The entire pulse length can be more efficiently utilized by varying the laser power to compensate for heat diffusion. Such a pulse can include an initial constant-power phase to bring the temperature up to a desired level and a slow decrease to maintain this temperature. While temperature is precisely constant at only one location in the retina, it varies little over a larger area. With such a pulse shape, a larger fraction of the pulse duration effectively contributes to the Arrhenius integral, which allows for a shorter pulse length to be used for coagulation at a given peak temperature (FIG. 5b).

Figure 5B:
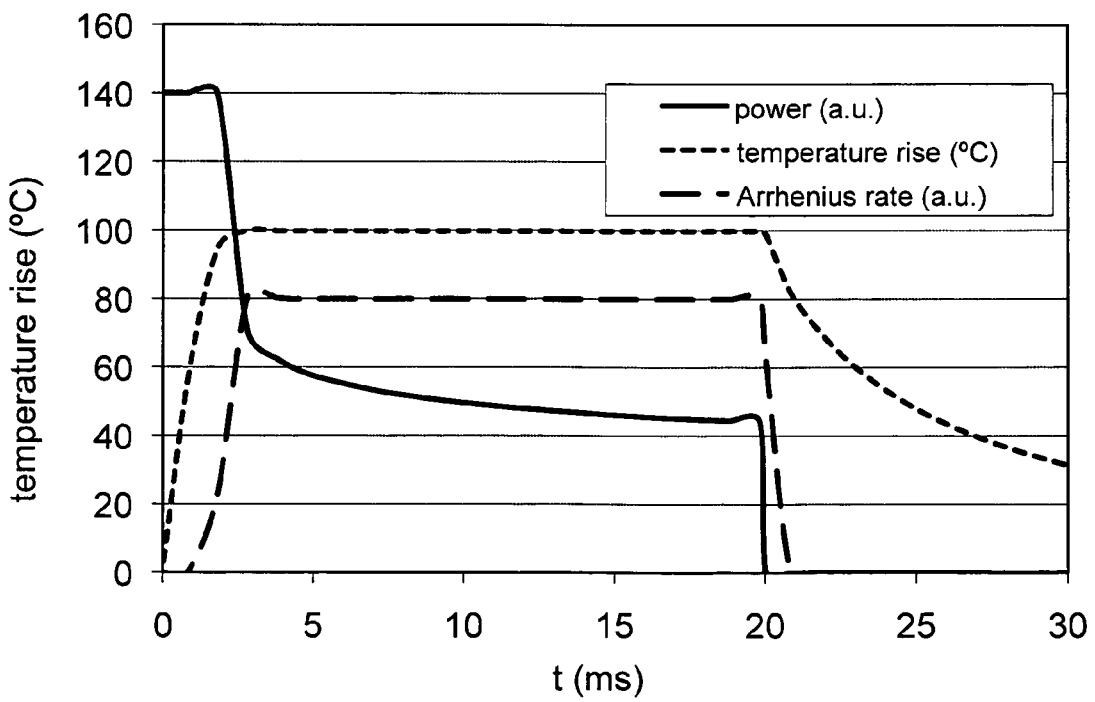

In the example of FIGS. 5a-b, a conventional square pulse (FIG. 5a) results in a slow temperature rise, where 95% of the Arrhenius integral occurs over the final 7 ms. A pulse shaped to maintain constant temperature (FIG. 5b) uses pulse duration more effectively. With this pulse shape, half the original duration can give the same Arrhenius integral with the same peak temperature.

Computational modeling of retinal heating allows for the determination of an optimal pulse shape which maintains constant temperature for a given pulse duration, beam size and peak temperature. Models can be refined to account for differences in heat deposition in various retinal layers, inhomogeneities due to pigmentation variation, and convective cooling due to perfusion. This refinement can be particularly important for optimizing the initial constant-power phase. Local heat source inhomogeneities produce duration-dependent overheating and are important for proper assessment of rupture thresholds.

We report the results of semi-analytical and finite-element modeling in conjunction with in vivo experimental verification of improvements in safety of retinal photocoagulation using pulses with modulated power.

C2. Methods

C2a. Pulse Shape Optimization

A simple semi-analytical model of retinal light absorption and heat conduction was constructed. This model approximated the posterior pole as three homogeneous layers, a 4 µm retinal pigment epithelium between the 100 µm neurosensory retinal and 70 µm choroidal layers. An axi-symmetric heat conduction model was coupled with an Arrhenius damage model. The Green's function solution to the heat conduction equation was numerically integrated in MATLAB® (v 7.4, MathWorks, Natick, Mass.) for the temperature rise at the top of the RPE in the beam center at the end of a pulse length $\tau$:

$$\Delta T(\tau) = \frac{k \cdot P}{2(\pi k)^{3/2} \cdot \rho c_p R^2} \int_0^\tau dt' \frac{f(t'-\tau)}{\sqrt{t'}} \left(1 - e^{-\frac{R^2}{4kt'}}\right) Z_{int}(t') \qquad (4)$$

where f(t) is the pulse shape normalized to unity, P is the laser power, R is the beam radius (assumed to be 60 µm, top-hat radial distribution), $\rho c_p$ is the density and heat capacity of water and $Z_{int}$ is an integral corresponding to energy deposition in the RPE and choroidal layers by the absorbed laser beam:

$$Z_{int}(t') = \alpha_1 \int_0^{z_{RPE}} dz' e^{-\frac{z'^2}{4kt'} - \alpha_1 z'} + \alpha_2 \int_{z_{RPE}}^{z_{CH}} dz' e^{-\frac{z'^2}{4kt'} - \alpha_2 z'} \qquad (5)$$

The absorption coefficients for the RPE and choroid ($\alpha_1$ and $\alpha_2$ respectively) and RPE thickness $z_{RPE}$ were taken from a more extensive finite-element retinal photocoagulation model.

The pulse shape included two distinct phases: a constant power phase (t<$\tau_1$) and a decreasing power phase ($\tau_1 \leq t \leq \tau$). Vectors f($\tau_1$, $\tau$) representing the pulse shape f(t) were constructed for pulse durations $\tau$ of 5, 10 and 20 ms and $\tau_1$ between 0.01·$\tau$ and 0.99·$\tau$. The decreasing power phase was approximated as a spline defined at 20 evenly spaced points. A multi-parameter numerical optimization was performed for spline points that minimized the mean-square error of computed $\Delta T(t)$ and constant temperature on the interval [$\tau_1$, $\tau$] for all ($\tau_1$, $\tau$) pairs considered.

To find the duration of the initial phase $\tau_1$ maximizing the therapeutic window, the thresholds of rupture and mild coagulation were estimated. Temperature rise of 143° C. was defined as a threshold of vaporization and retinal rupture, corresponding to a 180° C. temperature at vaporization and 37° C. ambient temperature in accordance with previous measurements. In calculating the powers that brought peak temperature up to this threshold, the $Z_{int}$ term was modified to include an 11 µm "hot-spot" of elevated absorption coefficient corresponding to pigmentation inhomogeneities. Mild coagulation thresholds were estimated as the power at each duration that brought the Arrhenius integral (Eqn. 3) up to corresponding Arrhenius value in the full finite-element model of retinal coagulation. Initial phase durations ($\tau_1$) of 3.3, 6.4, and 11 ms maximized the therapeutic window for pulse durations of 5, 10 and 20 ms, respectively, with pulses decaying down to 0.63, 0.71 and 0.76 of the peak amplitude along the optimized splines.

C2b. Optoelectronic Setup

A PASCAL® photocoagulator (Optimedica, Santa Clara, Calif.) provided optical radiation from a CW frequency-doubled (532 nm) Nd:YAG laser. The device included a modified slit lamp and optical system which telecentrically imaged the surface of a multimode step index optical fiber through a 2-axis scanner. Peak output power could be continuously varied from 10 to 2500 mW. A graphical user interface allowed clinical parameters including spot size, duration and power to be controlled, and a foot pedal activated the laser. This system was used to produce pulses of 5, 10 and 20 ms in duration with a 200 µm spot size in the aerial focal plane.

To achieve shaped pulses, a trigger signal from the photocoagulator was conditioned with a digital delay generator (DG535, Stanford Research Systems, Sunnyvale, Calif.) and used to gate the output of an arbitrary waveform generator (33120A, Agilent, Santa Clara, Calif.). A graphical user interface (LabView, National Instruments, Austin, Tex.) allowed for the pulse shape and amplitude from the waveform generator to be controlled. This interface was programmed with the optimal pulse shapes computed in MATLAB®. The shaped pulse was used as an input to the PASCAL® laser driver, which modulated the power of the laser pulse according to the input waveform. Rise time for the pulse was less than 600 µs and intensity variations during the initial phase of constant power were less than 10%. The photocoagulator was operated conventionally to produce square pulses for comparison.

C2c. Experimental Methods

11 Dutch Belted rabbits (weight 1.5-2.5 kg) were used in accordance with the Association for Research in Vision and Opthalmology Resolution on the Use of Animals in Ophthalmic and Vision Research, with approval from the Stanford University Animal Institutional Review Board. Ketamine hydrochloride (35 mg/kg), xylazine (5 mg/kg) and glycopyrrolate (0.01 mg/kg) were used for anesthesia. Pupil dilation was achieved by 1 drop each of 1% tropicamide and 2.5% phenylephrine hydrochloride, and topical tetracaine hydrochloride 0.5% was used for local anesthesia. Both eyes of each rabbit were treated with shaped and square pulse exposures to allow for direct comparison of the relative safety of each treatment on an eye-to-eye basis. Exposures of 5 and 10 ms were placed in one eye of each animal and 20 ms exposures were placed in the fellow eye.

The threshold powers of mild coagulation and rupture at each of these pulse durations were measured for the two pulse shapes. Between 12 and 36 separate lesions were administered per eye for each pulse shape and duration. Power was titrated to give clinical appearance between invisible outcome (no lesion) and rupture. A standard retinal laser contact lens (OMSRA-S; Ocular Instruments, Bellevue, Wash.) was placed onto the mydriatic eye using hydroxypropyl methylcellulose as a contact gel. Taking into account the combined magnifications of the contact lens and rabbit eye of 0.66 the aerial beam image of 200 µm corresponded to a retinal spot size of 132 µm.

The clinical appearance of the laser lesions was graded by one observer within 3 seconds of delivering the laser pulse by means of the following scale: barely visible, mild, intense, and rupture. A barely visible lesion (often referred to as a minimally visible lesion, or MVL) was one that just crossed the limit of clinical detection, whereas a mild lesion was described as one that produced some blanching but no whitening. An intense lesion had an area of central whitening, with or without a ring of translucent edema. A rupture was assumed when a vapor bubble or discontinuity in retinal architecture was visualized with or without bleeding. Threshold powers for mild coagulation and rupture were calculated by Probit analysis in MATLAB® 7.4. The results were analyzed in terms of mean improvement in safe therapeutic window.

C2d. Finite Element Computational Model of Retinal Coagulation

A finite-element model of retinal heating and coagulation in rabbit was used to estimate threshold power and safe therapeutic window for the experimental pulse shapes. This model approximated the retina as a series of homogeneous absorbing layers and coupled an axi-symmetric heat conduction model with an Arrhenius damage model. As opposed to the simplified semi-analytical model used to optimize the pulse shape, this model incorporated retinal absorption and scattering, a stratified choroid (choriocapillaris, pigmented choroid, unpigmented bottom choroid), experimentally measured in-eye beam shape and power transmission, and calculated the temperature and Arrhenius integral maps over the entire retinal thickness. This model was implemented using the COMSOL Multiphysics 3.5 computational package.

Two modifications to the original model were incorporated in this study. An approximation to the measured pulse shape was used to describe the temporal variation of the laser source. This included both an exponential rise-time of 600 μs and a fit to the measured decay. Additionally, a threshold for mild coagulation was computed, assuming that it occurred when an Arrhenius value of 1 was reached at a radius of 50 μm and depth of 5 μm, corresponding to destruction of photoreceptor outer segments at a radius large enough to be visible opthalmoscopically. As in the original model, rupture was computed as the power to bring peak temperature to 180° C. with the inclusion of a central 11 μm hotspot of elevated absorption coefficient.

C3. Results

Figure 6:
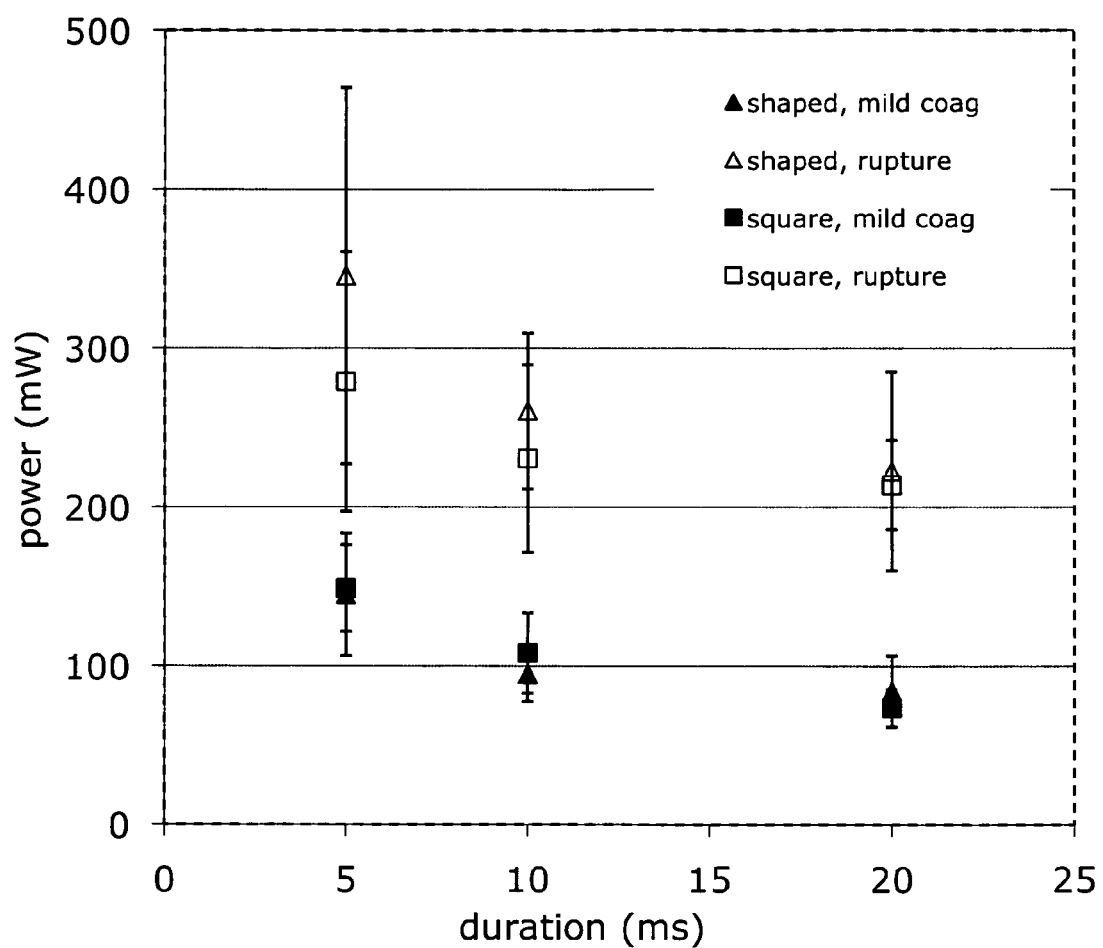
FIG. 6 shows thresholds for mild coagulation and for rupture for shaped and square pulses as a function of pulse duration.
Figure 7:
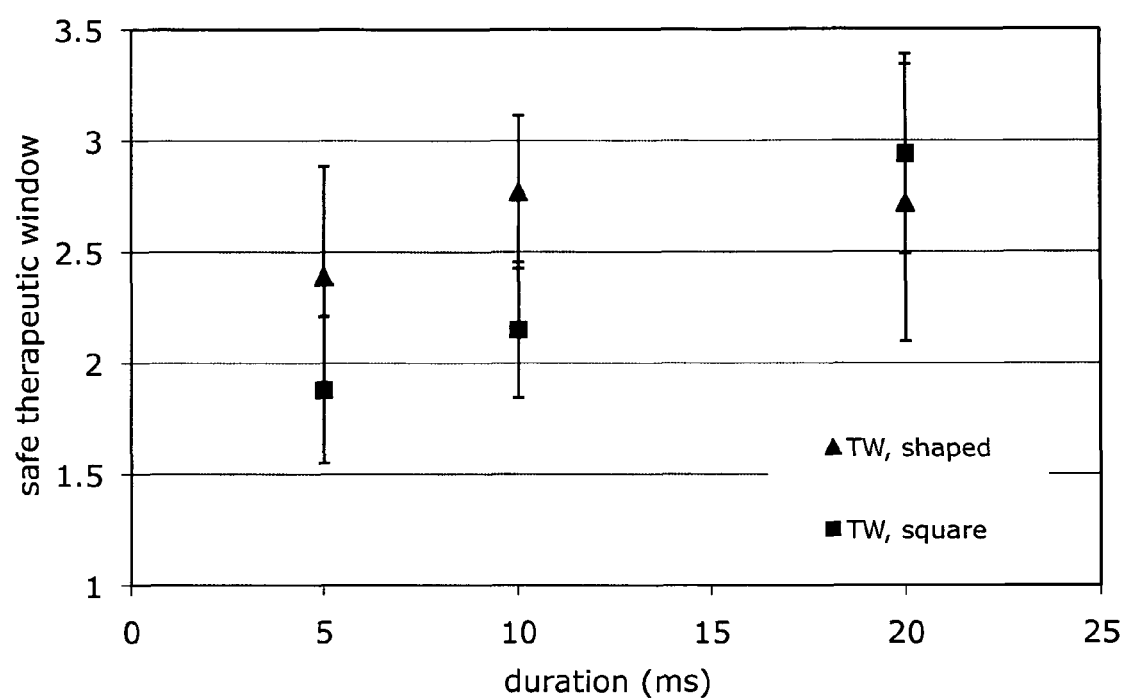
FIG. 7 shows safe therapeutic window as a function of pulse duration for square and shaped pulses.

Experimental threshold powers for mild coagulation and rupture are shown in FIG. 6. Error bars indicate standard deviation in threshold measurements over 11 experiments. The average Probit slope (ED84/ED50) for the threshold measurements was 1.15 for the shaped pulse and 1.10 for the square pulse. At shorter durations, the mean safe therapeutic window decreased for both pulse types (FIG. 7). A larger than expected improvement in therapeutic window was observed for the shaped pulses at 5 ms and 10 ms, while no significant difference in therapeutic window was observed at 20 ms.

Regarding statistical analysis of the data, it is important to keep in mind that the therapeutic window is expected to have a ratio distribution, with the underlying threshold laser powers following correlated normal distributions. This ratio distribution deviates significantly from normal; thus non-parametric hypothesis testing is preferable. A paired permutation test was performed in MATLAB® 7.4 for the null hypothesis that the measured therapeutic windows came from the same distribution. The increase in therapeutic window was found to be statistically significant ($p<0.003$) for 5 and 10 ms, while the observed decrease at 20 ms was not ($p=0.28$). The mean TW increase for 5 ms was +0.51 (95% CI: [0.31, 0.72]) while the increase for 10 ms was +0.61 [0.35, 0.88]. A small (7.5%) decrease in TW was measured for 20 ms pulse duration.

C4. Discussion

The current study was aimed at demonstrating the possibility of improved safety during sub-20 ms photocoagulation using a shaped laser pulse. The measured improvement in the safe therapeutic window for 5 and 10 ms pulse durations confirms this possibility. While the experimental pulse shapes used in this study were a close approximation to the computed optimal shapes, there are some additional significant aspects of the optimization and experimental implementation that should be considered.

The rise-time of the laser (600 μs) turned out to be significant relative to the short pulse lengths used. A refined model should take into account this limitation, and parametric optimization should be performed for the experimentally-attainable power profiles.

The simplified semi-analytical model used for optimizing the pulse shape was missing several aspects that affect the temperature distribution in the retina, namely, retinal absorption and scattering, a highly absorbing pigmented choroidal layer and a tapered irradiance distribution. The FWHM diameter of ~100 μm for the irradiance distribution used in the full finite-element model implies a heat diffusion time of 16.6 ms. This indicates that the temperature reaches a steady-state by the end of the 20 ms pulse, and thus the potential for improvement with pulse shaping should be minor. This was indeed confirmed by experiment—no significant improvement was observed for 20 ms pulses.

The threshold powers estimated by the computational model were found to be in general agreement with experimental data. In particular, computed rupture thresholds for the shaped pulse and coagulation thresholds for the square pulse were each within 8% of the measured values.

Practical clinical implementation of shaped-pulse photocoagulation may entail some modifications to the system used in this study. In diode-pumped solid state laser systems (such as the frequency-doubled Nd:YAG laser used in this work), adjustment of the laser power during the pulse can be performed with analog modulation of the laser pump current. This can be achieved with the insertion of a simple pulse-shaping circuit in the existing photocoagulation systems. More sophisticated approaches could use additional digital logic to allow for adjustment of the pulse shape to pulse duration.

Important clinical implications will arise if the measured improvement in safe therapeutic window can be duplicated in human subjects. As mentioned previously, due to pigmentation variation across the fundus, a safe TW of approximately three is required for any clinically applicable treatment. Photocoagulation with a shaped pulse of 10 ms has a therapeutic window similar to that of a 20 ms square pulse—approximately 2.8. The therapeutic window of 2.4 at 5 ms is also promising, and with further refinement of the pulse shape, this duration may also be made safe. Such reduction in pulse duration would allow for up to a four-fold increase in the number of lesions placed during eye fixation time with patterned scanning, reducing the overall treatment time by 75%. It would also further reduce heat diffusion into the neural retina and decrease perceived pain due to limited heat diffusion into the choroid, potentially resulting in a marked improvement over current photocoagulation settings.

The invention claimed is:

1. Apparatus for optical therapy, the apparatus comprising: a source of radiation; optics configured to receive radiation from said source and to provide an output treatment beam having an on-axis intensity minimum with an adjustable modulation depth; optics comprise a multi-mode optical fiber and coupling optics configured to couple radiation from said source to said optical fiber with an adjustable ratio of fundamental mode amplitude to higher order mode amplitude to provide said adjustable modulation depth; wherein said modulation depth of said intensity minimum is in a range from 0.1 to 0.9 of a maximum intensity of a spatial beam pattern of said treatment beam.

2. The apparatus of claim 1, further comprising:
a controller configured to provide said output treatment beam as a pulsed beam using optical radiation from said source;
wherein pulses in said treatment beam each include an early part preceding a late part, and wherein said early part has higher intensity than said late part.

3. The apparatus of claim 2, wherein said controller is configured to change said modulation depth during said pulses.

4. The apparatus of claim 2, wherein said controller is configured to change said modulation depth from one pulse to another pulse of said pulses.

5. The apparatus of claim 2, wherein said late part includes at least 20% of a duration of said pulses, and wherein said controller is configured to provide a pulse shape selected to provide a temperature rise at one or more points of said target tissue that is constant to within 10% during said late part.

6. A method of optical therapy, the method comprising: providing pulses of optical radiation to a target tissue;
wherein said pulses each include an early part preceding a late part, and wherein said early part has higher intensity than said late part; and
wherein said late part includes at least 20% of a duration of said pulses, and has a pulse shape selected to provide a temperature rise at one or more points of said target tissue that is constant to within 10% during said late part, further comprising providing said pulses of optical radiation as an output treatment beam having an on-axis intensity minimum with an adjustable modulation depth; wherein said modulation depth of said intensity minimum is in a range from 0.1 to 0.9 of a maximum intensity of a spatial beam pattern of said treatment beam.

7. The method of claim 6, further comprising adjusting an intensity ratio of said late part relative to said early part.

8. The method of claim 6, wherein said temperature rise is constant to within 10% during said late part at part or all of said target tissue illuminated by said optical radiation during said late part.

9. The method of claim 6, further comprising adjusting said modulation depth during said pulses.

10. The method of claim 6, further comprising adjusting said modulation depth from one pulse to another pulse of said pulses.

11. Apparatus for optical therapy, the apparatus comprising: an optical source; and a controller configured to provide a pulsed output treatment beam using optical radiation from said source,
wherein pulses in said treatment beam each include an early part preceding a late part; wherein said early part includes at least 10% of a duration of said pulses, has higher intensity than said late part, and has an intensity that is constant to within 10% during said early part; and wherein said late part includes at least 20% of said pulse and has an intensity that decreases during said late part, further comprising optics configured to receive radiation from said source and to provide said output treatment beam as a beam having an on-axis intensity minimum; wherein said modulation depth of said intensity minimum is in a range from 0.1 to 0.9 of a maximum intensity of a spatial beam pattern of said treatment beam.

12. The apparatus of claim 11, wherein said controller comprises a direct modulation circuit for said optical source.

13. The apparatus of claim 11, wherein said controller comprises an external modulator configured to receive radiation from said optical source and to provide said pulsed output treatment beam.

14. The apparatus of claim 11, wherein an intensity ratio of said late part relative to said early part is in a range from 0.1 to 0.9.

15. The apparatus of claim 11, wherein said controller is configured to change a modulation depth of said on-axis intensity minimum during said pulses.

16. The apparatus of claim 11, wherein said controller is configured to change a modulation depth of said on-axis intensity minimum from one pulse to another pulse of said pulses.

* * * * *